United States Patent [19]

Meadows et al.

[11] 4,379,178

[45] Apr. 5, 1983

[54] FINGERPRINTING SYSTEM

[75] Inventors: Louis B. Meadows, Valencia; Arthur S. Diamond, Ventura, both of Calif.

[73] Assignee: Dactek International, Inc., Van Nuys, Calif.

[21] Appl. No.: 248,275

[22] Filed: Mar. 27, 1981

[51] Int. Cl.³ .............................................. A61B 5/10
[52] U.S. Cl. .................................. 427/1; 118/31.5; 427/145
[58] Field of Search .................... 427/1, 145; 118/31.5

[56] References Cited

U.S. PATENT DOCUMENTS

| | | | |
|---|---|---|---|
| 3,960,632 | 6/1976 | Gaines et al. | 427/1 |
| 4,232,083 | 11/1980 | Buerkley et al. | 427/1 |
| 4,262,623 | 4/1981 | Smith et al. | 427/1 |

FOREIGN PATENT DOCUMENTS

| | | | |
|---|---|---|---|
| 43-052805 | 7/1968 | Japan | 427/1 |
| 428386 | 5/1935 | United Kingdom | 427/1 |

OTHER PUBLICATIONS

Jablonski, R. B. "Fingerprint Receptor Coating", in IBM Technical Bulletin, vol. 18, No. 6, Nov. 1975.

*Primary Examiner*—Michael R. Lusignan
*Assistant Examiner*—Janyce A. Bell
*Attorney, Agent, or Firm*—Marvin E. Jacobs

[57] ABSTRACT

Fingerprints images are formed by applying the distal portion 29 of a finger 32 to a porous pad 10 impregnated with a solution of marking compound. The finger portion may be prewetted or cleaned with cloth 30 impregnated with detergent solution. The finger 32 is then applied to a square 36 of a fingerprint card 38 impregnated with an aqueous solution of polyhydroxy developer such as 8-hydroxy-quinoline and propyl gallate containing a high molecular weight dibasic acid such as azelaic acid. A fingerprint image 40 immediately develops. Traces of the image can be removed with a cleaning solution impregnated cloth 42.

14 Claims, 5 Drawing Figures

FINGERPRINTING SYSTEM

TECHNICAL FIELD

The present inventions relate to an inkless fingerprint identification system and, more particularly, to a system and method for directly imaging fingerprints on a fingerprint card without the need for application of a fluid developer.

Since fingerprint patterns of ridge endings and ridge bifurcations do not vary with time for an individual and the pattern on each finger for any individual is unique and differentiates that individual from the rest of the society, fingerprint comparison is an absolute means of identification. This fact has been accepted by the scientific community and by the courts. Fingerprint identification is legally recognized forensic evidence of an individual's presence at a scene or association with property or instruments used in a crime. Fingerprint identification is also used commercially such as on identification cards for security systems, check identification means, and in many non-criminal government agencies.

Any reliable fingerprint identification system requires imaging a distinct print pattern on a substrate. Even in commercial identification systems such as with checks, it is important that the system be inoffensive to the subject. The early inking systems were difficult to utilize since it required much skill, training and care to provide a distinct print without ink running between ridges and obliterating substantial areas of the print image. Furthermore, the inking system was messy to use to both the operator and the subject requiring towelettes or a trip to a wash basin in order to remove the ink.

There have been several different inkless fingerprint systems proposed such as a magnetisable powder system disclosed in U.S. Pat. No. 3,831,552 or various imaging systems based on reaction between metal salts and polyhydroxy aromatic compounds. One very convenient implementation of this imaging reaction as an inkless fingerprinting system is the impregnation of a pad with one of the metal salts such as an iron chloride.

After the subject applies the distal surface of his finger against the pad to form a thin coating of the metal salt the finger is then pressed against the substrate such as a check or fingerprint card with a rolling motion. The substantially invisible fingerprint is then developed in a developer apparatus having a tray for receiving the card and an aerosol, pressurized container for dispersing a spray of developer onto the invisible fingerprint pattern.

The metallic salt on the card and the spray applied organic developing compound quickly react to form a colored compound which renders the fingerprint visible to form a permanent record. However, due to the belief that the accumulation of fluorocarbons in the stratosphere will deplete the ozone layer and cause excessive ultraviolet radiation on the surface of the earth, the U.S. Government has restricted and in some cases eliminated the use of fluorocarbons as a propellant.

DISCLOSURE OF THE INVENTION

An improved fingerprinting identification system is provided in accordance with the present invention. This system eliminates the use of propellants of any nature and does not require the spray application of developer. The system of the invention provides a dark, distinct fingerprint image as a permanent record of a substrate in a simple, efficient and reliable manner and uses techniques and materials familiar to operators of fingerprinting systems. The fingerprint image in the present invention develops rapidly and distinctly and forms a permanent record for use in any of the security or forensic procedures previously practiced in the fingerprinting field.

The method of producing a print of a finger or other body part comprises the steps of applying an aqueous solution of a color-forming, water-soluble, metal salt to the part to form an invisible, latent pattern, transferring said pattern to a card impregnated with 10 to 40 parts by weight of a mixture of at least one water-soluble compound capable of color developing said metal salt pattern selected from a quinolinol and a polyhydroxy compound with 1 to 10 parts by weight of a dibasic organic acid containing at least 6 carbon atoms, preferably 8 to 18 carbon atoms as a viscosity control agent. A dark image forms on said card as the metal salt pattern reacts with the developer compounds.

In accordance with the present invention, the chemical developer previously applied by spray is directly impregnated into the porous substrate. Therefore, on transfer of the metal salt pattern to the impregnated substrate a print of the finger ridge pattern will develop. There have been other attempts to develop a developer impregnated or coated card system such as U.S. Pat. No. 2,082,735. However, that patent requires that the trihydroxybenzoic acid be applied to the card as a coating, in a lacquer or other vehicle such as a glue-pigment composition. Lacquer coatings are not suitable for pre-printed cards because the solvent will dissolve the pre-inked matter such as the matrix of boxes for receiving the individual fingerprint impressions. Furthermore, a cured lacquer will ride on top of the surface as a shiny skin film which may tear or separate from the surface. Furthermore, the lacquer encapsulates the developer and renders unavailable some of the ink compound within the cured interior portion of the coating, leaving only the surface trihydroxybenzene compounds available for marking reaction with the metal salt.

It was therefore decided to attempt to prepare a card treated such that the marking compound would be impregnated into a surface layer or throughout the body of the card. In this manner, either uncoated or pre-inked stock could be used to form the dry-imaging fingerprint card of the invention. However, in early attempts to utilize such cards it was found that the cards worked well when fresh in that an image would develop very quickly or "pop up" so as to be visible within a short time after application of the metal salt carrying fingerprint to the card. However, if these cards were allowed to sit for a few days or a few weeks, the image would only slowly develop over a very long period of time. After much experimentation of the various additives to control penetration viscosity and marking ability, it was found that the addition to the impregnant of a high molecular weight dibasic acid containing at least six carbon atoms, preferably eight to eighteen carbon atoms, suitably azelaic acid provides an impregnating composition that results in a treated fingerprint card that gives instant imaging to form a distinct, very dark fingerprint image.

Another, unexpected result was the discovery that relatively low concentrations of azelaic acid, typically 2 to 5 percent by weight, were effective in adapting the solvent solution to be used as a printing "ink" or fluid. This feature is of special importance as it provides a fast, simple and economical means of coating, impregnating or imprinting cards of a variety of sizes with the trihydroxybenzene solution being deposited only in certain sharply defined areas, such as for example the rectangular section of a fingerprint card described by the points A-B-C-D in FIG. 3.

Other aspects of the invention relate to an improved pad composition in which the sawdust ingredient utilized in U.S. Pat. No. 3,960,632 is replaced with a very finely divided silicate material. Another aspect of the invention relates to the discovery that application of a detergent composition to the distal portions of the fingertips before application of the fingers to the pad containing the metal salt results in much darker, immediate imaging when the fingerprint patterns are transferred to the impregnated card.

These and many other objects in attendant advantages of the invention will become apparent as the invention becomes better understood by reference to the following detailed description when considered in conjunction with the accompanying drawings.

BRIEF DESCRIPTION OF THE DRAWINGS

Referring now to FIGS. 1 and 2, the applicator 10 for applying the solution of fingerprinting marking compound to a finger comprises a container 12 receiving a porous matrix 14 impregnated with marking solution. A reservoir of solution may be provided by disposing a porous resilient member 16 such as a felt disc in the bottom of the container.

Figure 1:
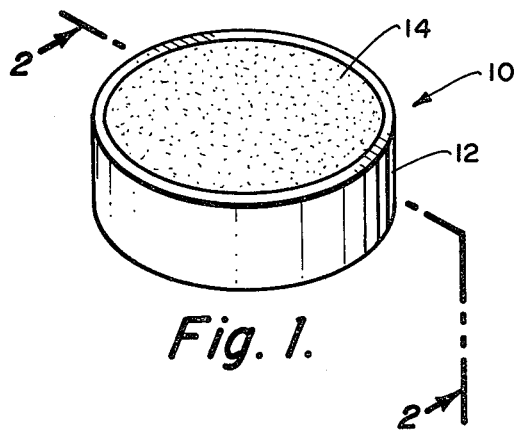
FIG. 1 is in a perspective view of the fingerprint marking solution impregnated pad from the invention.
Figure 2:
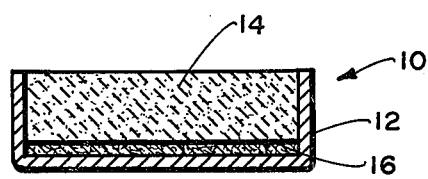
FIG. 2 is a sectional view taken along the line 2—2 of FIG. 1.

The porous pad member 14 is preferably fairly rigid so that only the ridges of the distal ends of the finger are wetted and moistened by the marking solution. The pad is formed of a material that is inert to the marking solution, either an inorganic material such as plaster or a porous plastic such as the UHMWPE plastic sheeting produced by The Porex Division of Glasrock (Fairburn, Ga.) or the Porelon plastic parts produced by The Porelon Inc. subsidiary of Johnson Way (Cookeville, Tenn.).

While both porous plaster and porous plastic pads have been found to work in accordance with the concept of this invention, the size of the microscopic pores have been observed to determine the sharpness, clarity or resolution of the resultant fingerprint image. Macroporous plastic pads, for example, which have pore openings or cells greater than 10 microns in diameter, produce a coarse fingerprint image wherein the cell structure is apparent and some detail is lost.

Microporous plastics and plaster pads molded in accordance with the present invention, have a much finer pore structure with openings less than 10 microns in diameter. These produce the clearest, sharpest prints in which every detail of the fingerprint ridge is preserved and no overall pore pattern is discernible.

A high porosity pad is formed by adding 1 to 10% of a finely divided silica, or a finely divided metal silicate absorbant such as diatomaceous earth to a white plaster formulation. The porous pad composition may also contain 0.1 to 2% of a coloring agent such as a red oxide dye. The dry ingredients are dispersed in about 100 to 500 milliliters of tap water on a dry basis. A suitable example of practice follows:

EXAMPLE 1

10 ounces of tap water are placed into a one-quart blender container and the blender turned on at low speed. 0.8 grams of Oxide Red No. 103 and 5 grams of HiSil T-600 silica are then added and blended at high speed for a minute. This red liquid is poured into a two-quart mixing bowl and 514 grams of white plaster is added slowly into the mixing bowl and stirred for two minutes. After the mixture has deaerated for one minute it is remixed for a minute and then poured into a suitable mold cavity on a vibrating table and vibrated for 15 to 20 seconds. The vibrator is then turned "off" and the felt pad is placed on the top of the mold. The pad is allowed to cure for about 35 minutes and then removed from the mold. The pad may be subjected to a final heat cure at a temperature of about 80°–150° F. for a period of about 2–20 hours under moderate air flow. The dried pad is then removed from the mold and placed in a container 12 in the inverted position with the felt layer 16 at the bottom. The pad 10 is now ready for impregnation with marking solution. The pad is totally immersed in the solution and should be soaked into the pad for a period of at least five days, preferably at least two weeks even though it appears to penetrate earlier.

The pad soaking solution comprises a solution of a water-soluble metal salt marking compound and a water soluble humectant. The solution may also contain a small amount of a wetting agent or detergent. The solution generally contains, on a relative basis, 20 to 100 parts by weight of humectant; 2 to 30 parts by weight of metal salt; and optionally 0 to 100 parts of water. A small amount of detergent such as 1 to 10 grams of Aerosol OT (75% AQ) may be added. The ingredients are mixed to form a clear solution which is then soaked into the pad and allowed to penetrate for at least 24 hours preferably at least 5 days as discussed. The solution enters the cells of the porous plaster matrix and the remainder is stored in the felt pad reservoir. The pad may be regenerated by resoaking after many hours of service. The pad can be formed of other materials such as rigid plastic foams and the like.

The soluble metal salt reactive with the hydroxyphenolic compound can be a metal from groups I to VIII of the periodic table and the anion may be inorganic such as halide, sulfate or ferrocyanide. A preferred marking ingredient, due to cost, availability, nontoxicity and safety, is ferric chloride. Ferric chloride may be used in a mixture with 5 1 to 30% of its weight of ferrous chloride. The solvent for the salt is preferably a liquid that does not evaporate under ambient conditions and also preferably as a humectant in order to keep the pad from drying out under normal conditions. Preferred solvent-humectants are materials such as glycerine, an alkylene glycol such as ethylene glycol or propylene glycol or various low molecular weight polyether liquids based on ethylene and/or propylene oxide. A suitable example of a pad soaking solution follows:

EXAMPLE 2

| Material | Amount |
| --- | --- |
| Glycerine | 23,866 grams |
| $FeCl_3 \cdot 6H_2O$ | 5,818 grams |
| $FeCl_2 \cdot 4H_2O$ | 763 grams |
| Aerosol OT | 8 ml |

Figure 4:
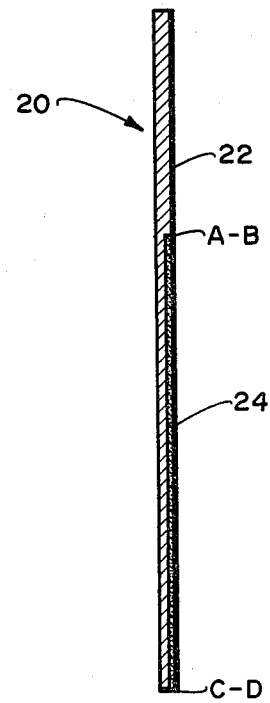
FIG. 4 is a sectional view taken along the line 4—4 of FIG. 3.
Figure 3:
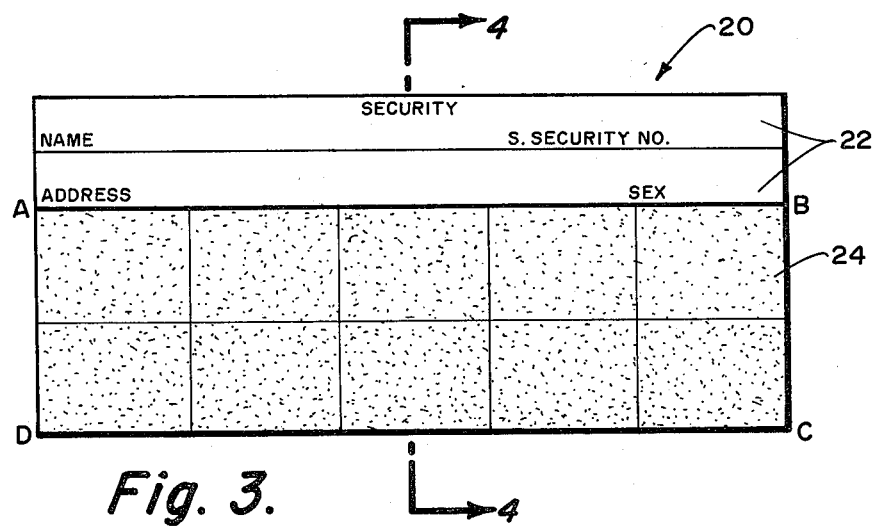
FIG. 3 is a front elevational view of a fingerprint card treated in accordance with the invention.
Figure 5A:
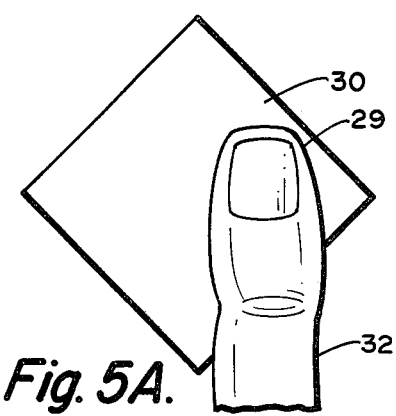
FIGS. 5A, B, C, D and E are schematic views of the steps utilized in preparing a fingerprint record in the system of the invention.
Figure 5B:
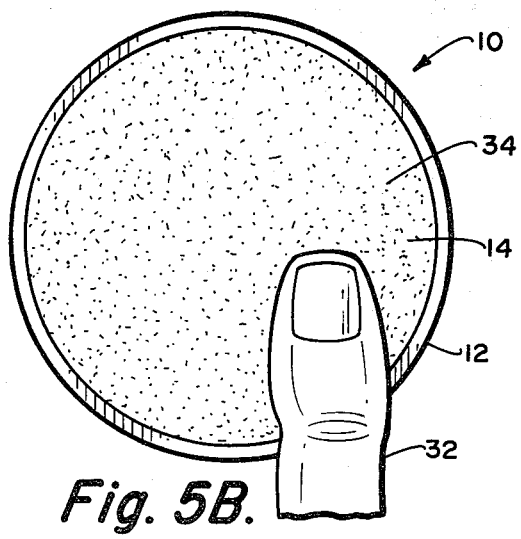
Figure 5C:
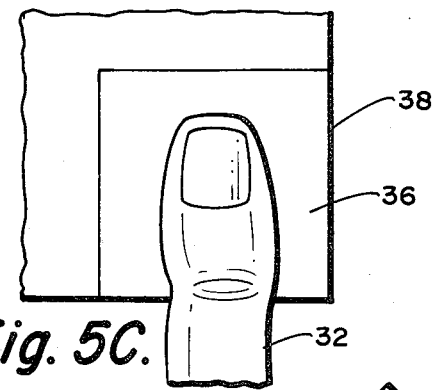
Figures 5D, 5E:
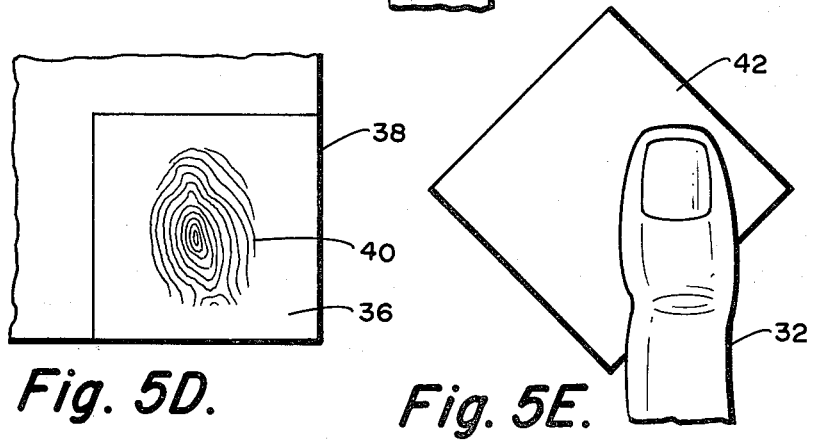

Referring now to FIGS. 3 and 4, the hydroxyaromatic compound that forms the marking reaction with the metal salt is impregnated into a substrate, suitably a fibrous substrate such as a paper check or ID card 20, by impregnation from solution. The card 20 will have a data receiving area 22 on the top portion thereof and a fingerprint matrix receiving portion 24 in the lower half thereof, bounded by points A-B-C-D. The marking solution need only be impregnated into the fingerprint portion 24 of the card.

The metal salt is preferably a salt of a transition metal such as iron, titanium, vanadium, chromium, magnesium, cobalt, nickel, copper, molybdenum, tungsten and the like with an anion such as ferride, citrate, sulfate, nitrate, stearate, acetate, formate, phosphate and the like.

The preferred marking ingredients are quinolinol derivatives, preferably 8-hydroxy-quinoline and various substitute derivatives thereof alone or in combination with a polyhydroxy phenol compound such as trihydroxy benzoic acid, pyrogallol, catechol, gallic acid, propyl gallate, and the like. The marking reaction should be such as to give a clear and distinct image, preferably a very dark, black colored image. The impregnating composition is formed as a solution in a common solvent. Solvents such as acetone are utilizable, however, for inhalation reasons and due to the tendency of acetone to dissolve preprinted areas of the fingerprint card, it is preferred to utilize an alcohol solvent, suitably a lower alkanol such as methanol, ethanol or mixtures thereof. The marking composition contains, based on 100 grams of solvent, 10 to 40 parts by weight of marking compound, and 1 to 10 parts of the higher molecular weight dibasic/acid additive of the invention. The composition may also contain from 0.1 to 3 parts of a finely divided silica as a thickener. The preferred composition contains a mixture of a trihydroxybenzene such as propyl gallate and 8-hydroxyquinoline in a ratio of at least five to one of the gallate to the hydroxy-quinoline, preferably at least ten to one. The preferred dibasic acid is azelaic acid. A card impregnating solution is made by heating the solvent gently with stirring to dissolve ingredients while maintaining a maximum temperature of 45° until the azelaic acid is dissolved, then removing the heat and adding the finely divided silica such as Cab-O-Sil, if desired.

A suitable example of practice follows.

EXAMPLE 3

| Material | Amount |
| --- | --- |
| Denatured alcohol | 1540 Ml |
| Propyl Gallate | 240 grams |
| 8-Hydroxy-Quinoline | 15.75 grams |
| Azelaic Acid | 60 grams |
| Cab-O-Sil M5 | 7.5 grams |

The cards are coated with this solution or preferably imprinted by means of the water fountain of an offset press on a basis of 0.01 to 10 pounds of impregnating solution for 3,000 square feet of cards. It has been determined that for normal cards and good imaging, the coating basis can generally be 0.5 to 1.0 pounds per 3,000 square feet of cards.

Many different dibasic fatty acids and fatty acid salts were investigated since impregnated cards, after aging for several weeks did not "pop up" (produce an image instantly) when the fingertip wetted with iron chloride solution was applied to them. A standard solution based on 205 (ml) by weight of denatured alcohol and 32 grams propyl gallate to 2.1 grams of 8-hydroxyquinoline was prepared. To each of these solutions was added 8 grams by weight of either stearic acid, palmitic acid, azelaic acid, or potassium oleate. All of these solutions, including a control solution without any additive, were coated onto standard FBI fingerprint cards. The card impregnated with the solution containing azelaic acid gave the darkest print. Potassium oleate also gave a dark image but the solution appeared to be unstable. The control image popped up when cards were freshly coated but developed slowly with cards that had been stored for several weeks. Impregnating solution for the card treated with the solution containing azelaic acid, when further modified to include 1 gram of Cab-O-Sil M5 (finely divided silica), gave a further improved fingerprint definition.

While the exact mechanism is unknown, by which fresh cards pop up and aged cards produce a fingerprint image that develops slowly, it is likely that the trihydroxybenzene, or other polyhydroxyphenolic compounds used, with time, gradually diffuse away from the surface into the body of the card stock making them less available for instant reaction.

Azelaic acid and other dibasic fatty acids that are soluble in the card coating solution appear to enhance or intensify the image, to serve as a carrier for the polyhydroxy phenolic reagents used, and to act as a filler or blocking agent. In this last role, the dibasic acid could conceivably fill the pores or interstices of the fingerprint card or other fibrous substrate, thereby preventing the reagent solution from diffusing away from the card surface.

Thus, the high molecular weight, dibasic acids of this invention appear to serve at least four unique functions: First, they act as an intensifier to increase the density of the fingerprint image; second, they serve as fillers or carriers to hold the color forming reagents at the fingerprint card surface keeping them available for instant reaction; third, they function as viscosity builders, solution thickeners, or tackifying agents to enable the reagent solution to assume the properties of a fluid ink, capable of being imprinted in well-defined areas by means of a printing process such as offset lithography; and, fourth, they prevent the freshly formed fingerprint from feathering, bleeding or blotting as the moist image is prone to do by virtue of the wicking action of paper fibers. This feathering problem has been a particular drawback with prior art inkless fingerprint solutions.

It was further discovered during the development of the invention that the darkness of the immediate fingerprint varied from time to time and with different operators. After investigation it was discovered that this usually occured when the surface of the pad was dry. This can be remedied by rewetting the pad with salt solution or, more conveniently and reliably, by prewetting the fingers with an aqueous solution of detergent prior to fingerprinting resulted in significant image enhancement. A convenient form of practicing such a step would be to impregnate the detergent solution onto a fibrous substrate such as paper or cloth. It is not known whether the image enhancement is a result of the wetting agent of the simple fact of pre-moistening of the finger before application to the pad or of the removal of natural oils from the skin surface which would repel the pad solution and therefore prevent application of a uniform layer on the finger. A suitable solution for use in impregnating the fibrous substrate would contain an aqueous solution of a suitable surfactant such as Triton X-100 or Aerosol OT. An example of a suitable solution follows:

EXAMPLE 4

| Material | Amount |
| --- | --- |
| Triton-x 100 | 1-2 grams |
| 10-15 less 1% | Isopropyl alcohol preservatives |
| remainder | and buffer water |

The process of the invention is an inkless system in terms of avoiding handling greasy conventional inks. However, the repeated use of the system within a short period of time may result in staining of the fingertips of the user or operator. It is therefore desirable to provide a cleaning solution to remove the stains. The cleaning solution may contain an organic solvent for the marking compound such as a non-hazardous alcohol suitably methanol, ethanol or propanol and a soluble metal chelating agent such as citric acid. The solution may also contain a surfactant. Again the cleaning solution can be conveniently impregnated into a fibrous substrate such as paper or cloth and can be cut into small pieces such as found in commercial hand wiping products. An example of a suitable solution follows:

EXAMPLE 5

| Material | Amount |
| --- | --- |
| Distilled water | 500 Ml |
| 2-Propanol | 400 Ml |
| Citric acid | 130 grams |
| Aerosol OT | 2 Ml |

We have found that the impregnated paper product previously described to pre-wet the fingers before use of the system may be utilized as the cleaning solution after use of the system if it is formulated to contain a marking compound solvent such as propanol.

Referring now to FIGS. 5A to 5E, the system of the invention may be provided in a kit form such that all parts may be integrated and used together in a cooperative mode. In a description of the complete use of the system, the distal portion 29 of a finger 32 is pre-wetted with a detergent solution impregnated into cloth 30. The wetted finger 32 is then applied to the top surface 34 of a marking compound impregnated, porous plaster or porous plastic pad 10. The finger of the subject 32 containing an invisible pattern of marking compound, is then applied to a correlated square 36 of a developer impregnated fingerprint card 38. A fingerprint pattern 40 immediately develops. The finger 32 of the user is then cleansed with a cleaning solution impregnated pad 42.

It is to be realized that only preferred embodiments of the invention have been described and that numerous substitutions, alterations and modifications are all permissible without departing from the spirit and scope of the invention as defined in the following claims.

We claim:

1. A method of producing a print of a finger or other body part comprising the steps of:
    applying an aqueous solution of a color-forming, water-soluble, metal salt compound to said part to form an invisible, latent pattern; transferring said invisible pattern to a card impregnated with 10 to 40 parts by weight of a developer for said metal compound comprising a mixture of at least one water-soluble color developing compound selected from a polyhydroxy aromatic compound, a quinolinol compound and mixtures thereof with 1 to 10 parts by weight of a viscosity control agent consisting essentially of a dibasic organic acid containing from 8 to 18 carbon atoms; and
    forming a dark image on said card by reacting said pattern of metal salt compound with said color-forming developer.

2. A method according to claim 1 in which the metal salt is dissolved in an aqueous solution impregnated into a porous pad and said solution also contains a humectant.

3. A method according to claim 2 in which the pad is a porous plaster containing a finely divided silica or metal silicate.

4. A method according to claim 3 in which the metal salt is an iron chloride.

5. A method according to claim 4 in which the iron chloride is a mixture of ferrous chloride and ferric chloride.

6. A method according to claim 2 further including the step of removing any developed image remaining on body part by wiping the body part with a fibrous substrate impregnated with a solvent for the developed image.

7. A method according to claim 1 in which the card is impregnated only in the fingerprint receiving area thereof.

8. A method according to claim 1 in which the developer compound comprises a mixture of a quinolinol and a trihydroxy phenol.

9. A method according to claim 8 which the acid is azelaic acid and the mixture comprises 8-hydroxyquinoline and propyl gallate.

10. A fingerprint imaging device comprising:
    a card having a first information receiving area and a second fingerpring receiving area;
    at least said second area being impregnated with a mixture of a water-soluble developer capable of developing invisible, latent patterns of water-soluble transition metal salts selected from at least one of a polyhydroxy compound and a quinolinol with 2 to 8 percent by weight of a water-soluble dibasic fatty acid containing from 8 to 18 carbon atoms.

11. A card according to claim 10 in which only said second area is impregnated.

12. A card according to claim 10 in which the mixture comprises 8-hydroxy-quinoline and propyl gallate.

13. A card according to claim 12 in which the dibasic acid contains 8 to 18 carbon atoms.

14. A card according to claim 10 in which the dibasic acid is azelaic acid.

* * * * *

UNITED STATES PATENT AND TRADEMARK OFFICE
CERTIFICATE OF CORRECTION

PATENT NO. : 4,379,178
DATED : April 5, 1983
INVENTOR(S) : Louis B. Meadows and Arthur S. Diamond It is certified that error appears in the above-identified patent and that said Letters Patent are hereby corrected as shown below:

Col. 4, l. 58, the words "5 1 to" should be -- 5 to --.

Col. 6, l. 65, the word "occured" should be -- occurred --.

Signed and Sealed this

Twenty-first Day of June 1983

|SEAL|

Attest:

DONALD J. QUIGG

Attesting Officer      Acting Commissioner of Patents and Trademarks